United States Patent
Wehnes et al.

(10) Patent No.: US 10,087,423 B2
(45) Date of Patent: Oct. 2, 2018

(54) METHOD FOR HARVESTING EXPRESSION PRODUCTS

(75) Inventors: Engelbert Wehnes, Berlin (DE); Uwe Werner, Panketal (DE); Christian Leschke, Panketal (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 22 days.

(21) Appl. No.: 13/811,093

(22) PCT Filed: Jul. 15, 2011

(86) PCT No.: PCT/EP2011/003552
§ 371 (c)(1),
(2), (4) Date: Mar. 19, 2013

(87) PCT Pub. No.: WO2012/010280
PCT Pub. Date: Jan. 26, 2012

(65) Prior Publication Data
US 2013/0183742 A1    Jul. 18, 2013

(30) Foreign Application Priority Data

Jul. 20, 2010 (EP) .................................. 10007510
Aug. 19, 2010 (EP) .................................. 10008676

(51) Int. Cl.
| | | |
|---|---|---|
| C07H 21/04 | (2006.01) | |
| C12N 7/00 | (2006.01) | |
| A61K 39/395 | (2006.01) | |
| A61K 48/00 | (2006.01) | |
| C12N 5/00 | (2006.01) | |
| C12N 7/02 | (2006.01) | |
| C12M 1/00 | (2006.01) | |

(52) U.S. Cl.
CPC ............... *C12N 7/02* (2013.01); *C12M 47/02* (2013.01); *C12N 7/00* (2013.01); *C12N 2710/24151* (2013.01)

(58) Field of Classification Search
CPC .... A61K 38/00; C07K 14/4748; C07K 16/32; C07K 2317/56; C07K 2319/00
USPC ........................................................ 435/239
See application file for complete search history.

(56) References Cited

U.S. PATENT DOCUMENTS

| 5,834,303 A | 11/1998 | Fujishiro |
| 2009/0325269 A1 | 12/2009 | Marschke |

FOREIGN PATENT DOCUMENTS

| WO | WO95/02049 | * | 1/1995 |
| WO | WO 95/02049 A1 | | 1/1995 |
| WO | WO9502049 | * | 1/1995 |
| WO | WO 03/070898 A2 | | 8/2003 |
| WO | WO 03/097797 A2 | | 11/2003 |
| WO | WO2004/022729 | * | 3/2004 |
| WO | WO 2005/080556 A2 | | 9/2005 |
| WO | WO 2006/052826 A2 | | 5/2006 |
| WO | WO2006052826 | * | 5/2006 |
| WO | WO2006108846 | * | 10/2006 |
| WO | WO 2008/066858 A2 | | 6/2008 |
| WO | WO 2008/138533 A1 | | 11/2008 |
| WO | WO 2009/100521 A1 | | 8/2009 |
| WO | WO 2009/157680 A1 | | 12/2009 |

OTHER PUBLICATIONS

European Search Report for EP Application No. 10 00 7510, dated Oct. 15, 2010.
International Search Report and Written Opinion of the International Searching Authority for PCT/EP2011/003552 A1, dated Oct. 14, 2011.
EPO Communication dated Jun. 21, 2016 EP application 11733805.3 (National Phase of PCT/EP 2011/003552).
EPO Communication dated Apr. 10, 2017 for EP application 11733805.3 (National Phase of PCT/EP 2011/003552).

* cited by examiner

Primary Examiner — Barry A Chestnut

(57) ABSTRACT

The present invention provides methods and systems for recovering an essentially cell-associated expression product from a host cell comprising (a) culturing said host cell under conditions that allow expression of said expression product; (b) collecting said host cell in/on a filter unit; (c) disrupting said host cell in/on the filter unit; and (d) separating said expression product from said disrupted host cell. The present invention also provides an expression product obtainable by the methods or systems, wherein the expression product is a poxvirus.

16 Claims, No Drawings

METHOD FOR HARVESTING EXPRESSION PRODUCTS

This application is a National Phase application under 35 U.S.C. § 371 of International Application No. PCT/EP2011/003552, filed Jul. 15, 2011, and claims the benefit under 35 U.S.C. § 365 of European Application No. 10008676, filed Aug. 19, 2010, and of European Application No. 10007510, filed Jul. 20, 2010, the disclosures of which are incorporated herein by reference in their entirety.

FIELD OF THE INVENTION

The present invention provides a method for recovering an essentially cell-associated expression product from a host cell comprising (a) culturing said host cell under conditions that allow expression of said expression product; (b) collecting said host cell in/on a filter unit; (c) disrupting said host cell in/on the filter unit; and (d) separating said expression product from said disrupted host cell. Said host cell is preferably a vertebrate cell, more preferably an avian cell, which is preferably cultured in suspension. Furthermore, the present invention provides for the use of a filter unit characterized in that said filter unit is (i) suitable to retain a host cell which expresses an expression product; and (ii) suitable for elution of said expression product from the filter unit after cell disruption in/on said filter unit for recovering said expression product from said host cell as well as for a system for recovering an expression product from a host cell comprising said filter unit. The present invention also provides an expression product obtainable by said method, said expression product being preferably a virus, specifically a poxvirus, in particular selected from the group consisting of fowlpoxvirus, vaccinia virus and, more preferably, modified vaccinia virus Ankara, MVA.

BACKGROUND OF THE INVENTION

The production of proteins in genetically engineered host cells is practiced since many years. Prokaryotic (bacterial) cells and eukaryotic cells such as yeast cells and mammalian cells are used for the production of therapeutic proteins or industrially useful proteins such as enzymes for the production of food, detergents and the like. In particular, protein production in eukaryotic, in particular mammalian cells is an important tool in numerous scientific and commercial areas. For example, the proteins expressed in and purified from mammalian cell systems are routinely needed for life science research and development. In the field of biomedicine, proteins for human therapy, vaccination or diagnostic applications are typically produced in mammalian cells. Gene cloning, protein engineering, biochemical and biophysical characterization of proteins also require the use of gene expression in mammalian cells. Other applications in widespread use involve screening of libraries of chemical compounds in drug discovery, and the development of cell-based biosensors.

A vast number of expression systems are used to produce recombinant proteins, ranging from cell free systems to cell based systems. Presently, due to technical limitations associated with cell free expression systems, cell based systems are more commonly used for recombinant protein expression. Cell based expression systems include those utilizing bacteria, yeast, insect cells or mammalian cells as hosts. The majority of these systems utilize inducible expression. For example, in a recent international collaboration to produce and purify over 10,000 recombinant proteins for use in structural biology, well over 90% of these proteins were produced using some form of inducible expression system (Nature Methods 5, 135-146).

Typical examples of expression systems and purification processes are described in WO 95/02049. Host cells are lysed in suspension culture, the lysate is applied to a filter such that the compound of interest, a nucleic acid, is bound by the filter while the remaining lysate is separated from the compound of interest. A similar disclosure is presented in WO 2008/066858, with the exception that host cells containing the compound of interest, a nucleic acid, are first lysed in suspension such that their outer membrane is destroyed and then lysed to destroy the nuclear membrane so as to release the nucleic acid from the nucleus. Thus, this PCT-application provides, so to say, a step-wise lysis of host cells in suspension to finally release the compound of interest. Another quite similar approach is disclosed in WO 03/070898. Specifically, a heterologous group of cells are lysed to release DNA from a first cell type so as to then collect unlysed cells which are subsequently subjected to lysis. This step-wise approach allows the isolation of DNA from different types of cells. WO 2009/157680 is a typical example for the isolation of DNA from bacterial host cells. These host cells are lysed to release their DNA on a hydrogel column in order to have it available for further steps such as genetic engineering. Prior to applying the host cells to the hydrogel column, these host cells are lysed in suspension culture. An almost identical approach is presented in U.S. 2009/0325269, with the exception that the host cells are repeatedly lysed in an apparatus so as to quantitatively release their DNA which is the desired target material. A further example for the isolation of DNA from host cells, in particular bacterial host cells, is described in U.S. Pat. No. 5,834,303. Bacterial host cells are lysed to release their DNA which is then subject to column chromatography in order to purify the DNA. All these documents have in common that they provide processes for recovering DNA, preferably from bacterial host cells or mammalian cells. However, none of these documents aims at the recovery of proteins, let alone viruses. This is so because for proteins and in particular for viruses other well-established processes are commonly applied such as homogenization, freeze-thawing or lysis in suspension followed by various filtration steps.

Eukaryotic cells such as mammalian cells and avian cells are frequently used for the production of viruses. The arising of new threats (avian flu, west nile virus, anthrax, pox disease, etc.) as well as the development of gene therapy has increased the need for producing and purifying poxviruses for prophylactic or therapeutic purposes, especially for viruses as vaccines. This is notably the case for the Modified Vaccinia Virus Ankara (MVA). This poxvirus which was initially used for vaccinating immunodeficient patients against smallpox is now also used as a vector for gene therapy purposes. MVA carrying the gene coding for Human Papilloma Virus (HPV) or Human Immunodeficiency Virus (HIV) antigens is also used as a vector for the therapeutic treatment of ovarian carcinoma and HIV, respectively.

Poxviruses are a group of complex enveloped viruses that distinguish them principally by their unusual morphology, their large DNA genome and their cytoplasmic site of replication. The genome of several members of poxviridae, including the Copenhagen vaccinia virus (W) strain (Goebel et al., 1990, Virol. 179, 247-266 and 517-563; Johnson et al., 1993, Virol. 196, 381-401) and the modified vaccinia virus Ankara (MVA) strain (Antoine et al., 1998, Virol. 244, 365-396), have been mapped and sequenced. W has a double-stranded DNA genome of about 192 kb coding for about 200 proteins of which approximately 100 are involved in virus assembly. MVA is a highly attenuated vaccinia virus strain generated by more than 500 serial passages of the Ankara strain of vaccinia virus on chicken embryo fibroblasts (Mayr et al., 1975, Infection 3, 6-14 Swiss Patent No. 568,392). Examples of MVA virus strains deposited in compliance with the requirements of the Budapest Treaty are strains MVA 572, MVA 575, and MVA-BN deposited at the European Collection of Animal Cell Cultures (ECACC), Salisbury (UK) with the deposition numbers ECACC V94012707, ECACC V00120707 and ECACC V00083008, respectively, and described in U.S. Pat. Nos. 7,094,412 and 7,189,536.

MVA-BN® is a virus used in the manufacturing of a stand-alone third generation smallpox vaccine. MVA-BN® was developed by further passages from MVA strain 571/572. To date, more than 1800 subjects including subjects with atopic dermatitis (AD) and HIV infection have been vaccinated in clinical trials with MVA-BN® based vaccines. The renewed interest in smallpox vaccine-campaigns with Vaccinia-based vaccines has initiated an increased global demand for large-scale smallpox vaccine production. Furthermore, the use of poxviruses as a tool for preparation of recombinant vaccines has additionally created significant industrial interest in methods for manufacturing (growth and purification) of native Vaccinia viruses and recombinant-modified Vaccinia viruses.

Cell lines have become a valuable tool for vaccine manufacturing. The production of some important vaccines and viral vectors is still done in embryonated chicken eggs or primary chicken embryo fibroblasts. Vaccinia Viruses-based vaccines have in general been manufactured in primary CEF (Chicken Embryo Fibroblasts) cultures. Vaccines manufactured in primary CEF cultures are generally considered safe as regards residual contaminants. First, it is scientifically unlikely that primary cell cultures from healthy chicken embryos should contain any harmful contaminants (proteins, DNA). Second, millions of people have been vaccinated with vaccines manufactured on CEF cultures, in accordance with various reports so far without any severe adverse effects resulting from the contaminants (CEF proteins and CEF DNA). There is, therefore, no regulatory requirement for the level of host cell contaminants in vaccines manufactured in primary CEF cultures, but for each vaccine the manufacturer must document its safety. The regulatory concern for vaccines manufactured in primary CEF cultures relates to the risk of adventitious agents (microorganisms (including bacteria, fungi, mycoplasma/spiroplasma, my cobacteria, rickettsia, viruses, protozoa, parasites, TSE agent) that are inadvertently introduced into the production of a biological product.

Viruses used in the manufacturing of vaccines or for diagnostic purposes can be harvested and purified in several ways depending on the type of virus. Traditionally, purification of pox viruses including Vaccinia viruses and recombinant-modified Vaccinia viruses has been carried out based on methods separating molecules by means of their size differences. To enhance removal of host cell contaminants (e.g. DNA and proteins), in particular DNA, the primary purification by means of size separation has been supplemented by secondary methods such as enzymatic digestion of DNA (e.g. Benzonase treatment). Most commonly, the primary purification of Vaccinia viruses and recombinant-modified Vaccinia viruses has been performed by sucrose cushion or sucrose gradient centrifugation at various sucrose concentrations. Recently, ultrafiltration has also been applied either alone or in combination with sucrose cushion or sucrose gradient purification.

In the current methods for purification of Vaccinia viruses, manufactured in primary CEF culture the level of CEF protein may be up to 1 mg/dose and the CEF DNA level may exceed 10 µg/dose of $1 \times 10^8$ as measured by the $TCID_{50}$. These levels are considered acceptable from a safety and regulatory perspective as long as the individual vaccine manufacturer demonstrates that the levels to be found in the Final Drug Product (FDP) are safe at the intended human indications. Due to the risk of presence of adventitious agents in vaccines manufactured in primary cell cultures and the associated need for extensive, expensive biosafety testing of each vaccine batch manufactured, there is a strong stimulus for the vaccine industry to change to continuous cell lines. Once a continuous cell line has been characterized the need for testing for adventitious agents of the production batches is minimal.

However, switching from primary to continuous cell culture for production of Vaccinia and Vaccinia recombinant vaccines is expected to impose stricter safety and regulatory requirements. In fact, the regulatory authorities have proposed new requirements for levels of DNA contaminants in vaccines manufactured using continuous cell lines (See Draft FDA guideline), which may be as low as 10 ng host-cell DNA/dose. To achieve such low level of host cell contaminants, new and improved methods for harvesting and purification are needed.

Thus far, host cells (in particular, CEF cells) for poxviruses are typically cultured in roller flasks (also known as roller bottles) or in cell factories (such as disposable fixed-bed bioreactors). Roller flasks are cylindrical screw-capped flasks mostly made of disposable plastic; reusable glass ones are still used occasionally. Each flask is typically about 1 to 1.5 liters in total volume. Typically, a flask is filled with 0.1 to 0.3 liters of culture medium for cell cultivation. A stack of flasks is placed on a roller, the flasks rotate on the roller rack at 1 to 4 rpm and are incubated in an incubator or an incubation room. Roller flasks are used for the cultivation of both suspension cells and adherent cells. Roller flasks are only used in small scale when, for example, convenience and/or an aseptic production dictates this selection of cultivation methods. However, since culturing in roller flasks is cost intensive, tedious and not readily and conveniently scalable by keeping GMP-principles of aseptic processing to large scale production, manufacturers sought and are still seeking alternatives.

As an alternative to cultivation in roller flasks, host cells for poxviruses can also be grown by the use of the WAVE Bioreactor™ system. This system is a cell culture device suitable for applications in animal, virus, insect, and plant cell culture in suspension, or on microcarriers, as well as cellular therapeutics. The WAVE Bioreactor™ system consists of two components: disposable cell bags and a rocker. Culture medium and cells only contact a presterile, disposable chamber called a cellbag that is placed on a special rocking platform. The rocking motion of this platform induces waves in the culture fluid. These waves provide mixing and oxygen transfer, resulting in a perfect environment for cell growth that can easily support over $10 \times 10^6$ cells/ml.

Typically, when grown in roller flasks, cells adhere to the walls of the roller flask. The cells can be detached from the walls, for example, mechanically or enzymatically (such as trypsinization). Subsequently, host cells can be subjected to ultrasound treatment or high-pressure homogenization to obtain a homogenate (see WO 2003/054175) which can be further purified.

Alternatively, in order to release viruses from their host cells, culture medium is discarded (poured off) from roller flasks and cells are lysed, typically by way of a hypotonic lysis buffer. Subsequently, the mixture of lysed cells and viruses released from said cells are subject to filtration in order to obtain the released viruses. Thus, cell lysis takes place in the roller flasks. One can imagine that the afore-described process is highly susceptible to become non-aspectic, since roller flasks have to be opened to discard culture medium and to add cell lysis buffer. After that, they have to be re-opened once more in order to then obtain the released viruses by filtration such as depth filtration (see WO 2006/052826, in particular Example 2).

Though culturing host cells for poxviruses in cellbags of the WAVE Bioreactor™ system is attractive, since the culture can be conveniently kept aseptic and the process is readily scalable, the process of harvesting and purifying poxviruses may be somewhat inconvenient and thus not desirable insofar that potentially measures non-optimal for aseptic processing may have to be taken such as batch centrifugation or flow-through centrifugation of the host cells in order to harvest them. This is so because, in cellbags host cells do not grow adherently, but in suspension and, thus, culture medium cannot easily be discarded prior to cell lysis in order to release viruses. Accordingly, cells must be separated and thereby concentrated. However, batch centrifugation includes open process steps which are non-optimal for aseptic processing. Flow-through centrifugation, on the other hand, might not remove the complete cell culture medium, because the cells have to remain suspended to be able to remove them from the flow-through centrifuge at the end of the centrifugation. If cell culture medium is not removed completely, residual salt content might impair efficiency of subsequent processes, such as a subsequent hypotonic lysis step which probably results in a final product with insufficient yield (e.g. virus titer) and elevated impurity level.

Thus, in essence, in order to produce expression products such as therapeutic proteins or viruses for vaccination purposes under GMP standards including aseptic processing in large (industrial) scale, it is desirable to grow host cells in suspension in, for example, cellbags because of their advantageous properties (e.g., ideal aseptic environment for cell growth in high density culture). However, cells in suspension (e.g. in cellbags) may be disadvantageous, since harvesting and disrupting host cells may not be practicable in a closed process which retains an optimal yield.

Accordingly, there is a need for means and methods to harvest host cells, preferably grown under GMP and principles of aseptic processing, preferably in a closed process and to then release their intracellular or cell-associated expression product, also under said GMP-principles, and concomitantly obtaining the maximum yield of said expression product, preferably in the absence of impurities such as cell debris and/or culture medium. Hence, it is an aim of the present invention to comply with these needs and to thus provide a solution to the existing problem.

DESCRIPTION OF THE INVENTION

The present invention addresses the needs set out in the prior art and thus provides as a solution means and methods for recovering intracellular or essentially cell-associated expression products expressed by appropriate host cells by collecting said host cells (preferably eukaryotic host cells, preferably grown in suspension culture expressing said expression product) in/on a filter unit; disrupting said host cells in/on the filter unit; and separating said expression product from said host cells.

Generally, the filter unit is suitable to separate cell culture medium from host cells expressing said expression product. By that, host cells are recovered (enriched) from the cell culture medium and potential impurities contained in the cell culture medium are removed. Of note, the separation of the host cells from the cell culture medium is preferably done in a closed process and, thus, the separated host cells can be further processed in a closed process which is highly advantageous, since contamination due to open process steps can be avoided.

In addition, the filter unit is also generally suitable to allow disruption of said host cells in/on said filter unit.

In some preferred embodiments the filter unit is suitable to separate said expression product from said host cells after said expression product is released from said host cells after their disruption in/on the filter unit. In particular, the filter unit is capable of separating the expression product from disrupted cells if the pore size and/or structure of the filter unit is such that disrupted host cells (including cell debris, cell fragments, etc.) cannot pass the filter, while the expression product can, when being eluted from said filter unit. Accordingly, in that embodiment the disruption and separating step coincide, i.e., the disruption step includes the separation step. The skilled person is readily in a position to select a suitable filter medium that can be applied in that embodiment. This embodiment is contemplated to be applicable if the expression product is a molecule having a small size such as a small protein or a nucleotide sequence.

In other preferred embodiments the filter, apart from being suitable to separate said host cells from cell culture medium, allows elution of the expression product after said expression product is released from said host cells by disrupting said host cells (preferably by lysis) in/on said filter unit. In particular, the pore size and/or structure of the filter unit is such that disrupted host cells (including cell debris, cell fragments, etc.) are not essentially retained in/on said filter unit since the pore size and/or structure of said filter unit must be chosen such that it allows passing through of said expression product because of the size and/or structure of the expression product. Accordingly, it is inevitable that, apart from the expression product, also cell debris, cell fragments or the like pass through the filter, at least when the expression product is preferably eluted from said filter unit. That being said, it is also envisaged that some host cells are nevertheless retained in/on said filter unit. For example, they may not be totally disrupted and, thus, their size is still to large to pass the filter unit or cell debris forms aggregates which cannot pass the filter unit.

Cell debris, cell fragments or the like, which pass through the filter unit and are thus eluted together with the expression product, are separated from the expression product, for example, by a further purification step as described herein below. This embodiment is contemplated to be preferably applicable if the expression product is a virus, preferably a virus selected from the group consisting of fowlpox, vaccinia and modified virus Ankara (MVA).

Put it differently, the present invention provides, so to say, an all-in-one process including culturing host cells expressing an expression product, collecting said host cells in/on a filter unit and releasing said expression product in/on said filter unit by disrupting said host cells, thereby obtaining said expression product, wherein said process is preferably a closed aseptic process.

Hence, the decisive modification that the present inventors made is that the expression product of host cells collected in/on a filter unit is released in/on said filter unit by disrupting (preferably lysing) said host cells in/on said filter unit. As a result, the expression product can be directly obtained. In fact, it was surprisingly observed that host cells, in particular vertebrate cells, more preferably mammalian or avian cells, though they may be "stacked" and/or arranged in tiers in/on the filter unit and might thus not be sufficiently amenable to cell disruption because of shielding effects and/or accessibility issues, can be as sufficiently disrupted, preferably lysed, as can be achieved by prior art methods (see Example 3). Thus, the present inventors did not only find a fast, cost-efficient and scalable alternative method for recovering an expression product, but also a method that can be performed as/in a closed process—something that the prior art did not envisage.

By performing the method of the present invention, there is no need to first concentrate host cells by open steps and/or inefficient processes such as batch or flow-through centrifugation to then lyse said host cells. Rather, the means and methods of the present invention allow a one step procedure which is deemed to be advantageous, since optimal aseptic processing can be retained from culturing host cells up to their down-stream processing, thereby obtaining a satisfying yield of the host cells' expression product, preferably with the least possible amount of impurities.

The embodiments which characterize the present invention are described herein, shown in the Figures, illustrated in the Examples, and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", or and "all or any other combination of the elements connected by said term".

The term "about" or "approximately" as used herein means within 20%, preferably within 10%, and more preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The present inventors, with the aim of transferring the process for the production of a desired expression product by host cells from adherent or even suspension cell culture (e.g., in roller flasks) to suspension culture (e.g. in cell bags) in order to optimize both costs and efficiency of cell growth and thus production, had to solve the problem of harvesting and subsequently disrupting the host cells by retaining GMP-principles of aseptic processing and achieving low levels of impurities.

As explained above, it is nearly impossible to harvest and disrupt host cells by the use of the process that is applied when host cells are cultured in adherent culture (e.g. in roller flasks) and thereby retaining GMP-principles of aseptic processing and achieving a satisfying yield and purity of the expression product. Accordingly, the present inventors with the further aim of retaining GMP-principles of aseptic processing and obtaining a good yield of the expression product when harvesting and disrupting host cells grown in culture (including adherent and suspension culture, with suspension culture being preferred) found that it is, despite their expectations, possible to efficiently disrupt host cells collected on/in the filter unit that is also used to collect the host cells from the suspension culture (e.g. cell bags), i.e., a all-in-one process which does not require many steps and is thus almost insusceptible to contamination and/or impurities. As used herein, "impurities" or "contaminants" cover any unwanted substances which may originate from the host cells used for the expression of the expression product, for example, virus growth (e.g. host cell DNA or protein) or from any additives used during the manufacturing process including upstream and downstream (e.g. cell culture medium or supplements).

This finding paves the way for culturing host cells, in particular eukaryotic cells, preferably mammalian or avian cells, preferably in suspension, while preferably retaining GMP-principles of aseptic processing when harvesting said host cells and disrupting them in order to release and thus harvest their intracellular or cell-associated expression product.

That being so, the means and methods of the present invention are generally applicable to recover a desired expression product, preferably an intracellular or cell-associated expression product, from host cells, preferably grown in suspension culture, by collecting said host cells on/in a filter unit; disrupting said host cells in/on said filter unit, whereby said filter unit is preferably (i) suitable to retain said host cells and (ii) suitable to separate said expression product after cell disruption in/on said filter unit, thereby recovering said expression product; and separating said expression product from said host cells.

Put it differently, there is no restriction on certain host cells, as different cell types (bacterial, fungal or eukaryotic cells) could be used though eukaryotic host cells are preferred, vertebrate and insect cells are more preferred and with mammalian or avian hosts being particularly preferred. Further, there is no restriction on the expression product either, though intracellular and/or cell-associated expression products are preferred. Particularly preferred are viruses, more preferably are poxviruses and particularly preferred is MVA.

Accordingly, in a first aspect, the present invention provides a method for recovering an essentially cell-associated expression product from a host cell comprising
(a) culturing said host(s) cell under conditions that allow expression of said expression product;
(b) collecting said host cell(s) in/on a filter unit;
(c) disrupting said host cell(s) in/on the filter unit; and
(d) separating said expression product from said disrupted host cell(s).

Preferably, said expression product recovered in the above method is a virus, preferably a poxvirus, more preferably a virus selected from the group consisting of fowlpox virus, vaccinia virus and modified vaccinia virus Ankara (MVA).

The thus recovered (obtained) expression product may preferably be subject to a method for the preparation of a pharmaceutical composition comprising admixing said expression product with a pharmaceutically acceptable carrier.

Though less preferred, said expression product might contain remnants of the host cell such as cell debris, proteins or DNA. Such remnants might be present in a preparation comprising said expression product in trace amounts such as 5, 4, 3, 2, or 1% (v/v). Also, said preparation might additionally comprise components of a virus as described herein. Preferred components are detached envelopes, cleavage products of viral envelopes or aberrant forms of said envelopes of the viruses.

The filter unit is preferably characterized in that said filter unit is suitable to retain said host cell, thereby separating said host cells from the cell culture medium (giving rise to "filtrate 1" or "eluate 1"). The filter unit is preferably suitable to separate said expression product from said host cells after cell disruption in/on said filter unit, thereby retaining disrupted host cells and recovering said essentially cell-associated expression product which is allowed to pass through said filter unit, thereby said expression product being recovered in the flow through (i.e, it is then present in "filtrate 2" or "eluate 2").

Said filter unit has thus preferably a pore size and/or structure that is small enough to retain disrupted host cells, but to allow passing through of said expression product.

Alternatively, the filter unit is preferably suitable to allow passing through of and/or eluting said expression product from said host cells after cell disruption in/on said filter unit, thereby recovering said essentially cell-associated expression product which is allowed to pass through said filter unit (i.e., it is then present in "filtrate 2" or "eluate 2").

In order to achieve that the expression product passes through the filter unit after disruption of the host cells, it is preferred that a solution (preferably a lysis buffer as described herein) is applied, i.e., the expression product is eluted from said filter unit. Of course, if disruption of the host cells is achieved by lysis, the solution applied for said lysis, may already elute the expression product from the disrupted host cells. Hence, the disruption step is, so to say, coupled with the elution step. Nevertheless, an additional elution may be applied.

The recovered expression product can then be further separated from disrupted host cells (cell debris, cell fragments, cell organelles, host cell proteins or the like) which, because of the pore size and/or structure of said filter unit also pass through said filter unit. Said filter unit has thus preferably a pore size and/or structure that allows passing through of said expression product, but preferentially retains disrupted host cells. However, in view of the fact that the pore size and/or structure of said filter unit is dictated by the size of the expression product, it is inevitable that cell debris, cell fragments or the like also pass through said filter unit. Nevertheless, as mentioned above, separation of the expression product from said disruptured host cells can readily be achieved by a further purification step as described herein below.

The above being said, it is a preferred embodiment of the method of the present invention that the filter unit is suitable to retain said host cell, whereby said host cell is separated from cell culture medium.

It is also a preferred embodiment of the method of the present invention that the filter unit is suitable to allow disruption of said host cells in/on said filter unit.

It is also a preferred embodiment of the method of the present invention that the filter unit is suitable to allow passing through of and/or eluting the expression product from said host cell after cell disruption in/on said filter unit.

It is also preferred that the filter unit is further suitable to allow passing through of a disrupted host cell.

It is also a preferred embodiment of the method of the present invention that the filter unit is suitable to separate the expression product from said host cell, thereby retaining said disrupted host cell and allowing passing through of and/or eluting of said expression product.

It is also a preferred embodiment of the method of the present invention that the filter unit is suitable to separate the expression product from said host cell, thereby retaining said expression product and allowing passing through of and/or eluting the disrupted host cell.

It is an alternatively preferred embodiment of the method of the present invention that the filter unit is suitable to separate the expression product from said host cell, thereby retaining said disrupted host cell and said expression product and allowing passing through of and/or eluting the expression product.

It is another alternatively preferred embodiment of the method of the present invention that the filter unit is suitable to separate the expression product from said host cell, thereby retaining said disrupted host cell and said expression product and allowing passing through of and/or eluting the expression product and/or the disrupted host cell.

When host cells are disrupted as described herein, they are inevitably "disrupted host cells". "Disrupted host cells" are no longer intact, i.e., at least their cell membrane (or wall, respectively) is ruptured so that the host cells are leaking out. Accordingly, when used herein "disrupted host cells" encompass cell debris, cell fragments, cell organelles, host cell proteins, DNA, RNA and the like.

The cell-associated expression product is, preferably, within or attached to the host cell, as is further explained and described herein. As mentioned above, it is desirable that an expression product can be recovered from a host cell as applied in the present invention under GMP in an aseptic closed process step. Hence, it is a preferred embodiment that the methods of the present invention are used for recovering an expression product from a host cell under principles of GMP/optimal aseptic processing.

"Aseptic processing" or "aseptic method/process" means a procedure that is performed under sterile conditions, i.e., the methods of the present invention are protected by appropriate means and/or methods against contamination and/or cross contamination such as contamination by bacteria or viruses or other harmful agents for a subject, in particular a mammal, e.g. a human. For example, the methods of the present invention may be performed under a laminar flow hood or any other suitable means to protect the methods against contamination and/or cross contamination. Performing the methods of the present invention under sterile conditions includes inoculation, cultivation, collection, harvest and/or disruption of the host cells applied in the methods of the present invention. More preferably, the methods of the present invention are performed in accordance with the FDA Guidance for Industry—Sterile Drug Products Produced by Aseptic Processing—Current Good Manufacturing Practice (September, 2004) and/or Annex 1 to EU-GMP-Guide. The method of the present invention (when used herein the term "method" may be replaced by the term "process", thus both terms can be equally used) is thus preferably for an aseptic manufacturing method or process, specifically for pharmaceuticals, in particular vaccines.

It is thus preferably envisaged that all steps of the methods of the present invention are carried out aseptically. More preferably, the term "aseptic" when used herein means that the methods of the present invention for recovering an expression product as described herein are performed as a closed process. A "closed process" or "closed" means that the methods/processes of the present invention are performable in a way that external factors have essentially no or only minimal influence on the method steps, i.e., that external factors do not contaminate the methods (including culturing, collecting, disrupting host cells, separating and/or recovering the expression product) of the present invention and/or render the methods aseptically. "External factors" are all sources of contamination and/or sources having a potential contaminating influence on the methods of the present invention such as contaminated air, contaminated containers, valves, flexible tubes and the like, i.e., technical equipment applied for performing the methods of the present invention. "External factors" also include organisational measures such as (technical) staff that could also contaminate the methods of the present invention. Accordingly, a "closed process" is preferably performed in a way that the methods of the present invention are performed such that from culturing of host cells up to the separation (and recovery, optionally further purification) of the expression product (i.e., all method steps), external factors cannot influence the methods, since all steps are performed under closed conditions, i.e., the method is protected by (appropriate) technical and/or organisational means and/or measures against contamination and/or cross-contamination, preferably as described in the EG-GMP-Guide 5.19 (Cross-contamination should be avoided by appropriate technical or organisational measure, for example: f) using "closed systems"). Hence, the methods of the present invention are in a particularly preferred embodiment performable in the form of a closed system. Accordingly, the technical equipment required for performing the methods of the present invention in the form of a closed system is thus preferably pre-sterilized and, if run, means and/or measures are taken to protect the closed system from being contaminated and/or cross-contaminated.

It is furthermore highly desirable that the expression product is recovered in satisfying amounts. Accordingly, the methods of the present invention are preferably scalable. In particular, the methods of the present invention are preferably scalable (preferably while retaining GMP-principles of aseptic processing) when the expression product is a virus, preferably a poxvirus such as MVA. Scalable includes lab-scale, pilot-scale and industrial scale.

As used herein, "lab-scale" comprises virus preparation methods of providing less than 5,000 doses of $1.0 \times 10^8$ virus particles (pfu) (total less than $5.0 \times 10^{11}$ virus particles) per batch (production run).

As used herein, "pilot-scale" comprises virus preparation methods of providing more than 5,000 doses of $1.0 \times 10^8$ virus particles (pfu) (total more than $5.0 \times 10^{11}$ virus particles (pfu)), but less than 50,000 doses of $1.0 \times 10^8$ virus particles (pfu) (total minimum $5.0 \times 10^{12}$ virus particles (pfu)) per batch (production run).

As used herein, "industrial scale" or large-scale for the manufacturing of Vaccinia virus or recombinant Vaccinia virus-based vaccines comprises methods capable of providing a minimum of 50,000 doses of $1.0 \times 10^8$ virus particles (pfu) (total minimum $5.0 \times 10^{12}$ virus particles (pfu)) per batch (production run). Preferably, more than 100,000 doses of $1.0 \times 10^8$ virus particles (pfu) (total minimum $1.0 \times 10^{13}$ virus particles (pfu)) per batch (production run) are provided.

The term "recovering" in all its grammatical forms includes that an expression product is obtained, harvested, achieved, received or gained from a host cell which expresses said expression product. Said term—though being less preferred—also encompasses that the expression product may be isolated and/or further processed, for example, it may be purified, for example, by means and methods known in the art and/or described elsewhere herein. Moreover, said term also includes that host cells are disrupted to release the expression product, preferably to such an extent that further purification of the poxvirus becomes feasible.

The term "expresses" when used in the context of a host cell which expresses an expression product includes that the host cells produces the expression product. For a host cell to produce the expression product, transcription and/or translation has to occur within a host cell. Accordingly, the term "expression" also includes transcription and/or translation. The level of expression of a desired expression product in a host cell may be determined on the basis of either the amount of corresponding mRNA that is present in the cell, or the amount of the desired product encoded by the selected sequence. For example, mRNA transcribed from a selected sequence can be quantitated by PCR or by northern hybridization. Protein encoded by a selected sequence can be quantitated by various methods, e. g., by ELISA, by assaying for the biological activity of the protein, or by employing assays that are independent of such activity, such as western blotting or radioimmunoassay, using antibodies that recognize and bind to the protein.

An "expression product" is the product that is generated by a host cell. In a preferred embodiment of the present invention, the expression product is a proteinaceous product. "Proteinaceous" when used herein refers to any of a group of complex organic macromolecules that contain carbon, hydrogen, oxygen, nitrogen, and usually sulfur and are composed of one or more chains of amino acids. A preferred proteinaceous expression product is a polypeptide (of interest). Accordingly, the term "proteinaceous" also means relating to, consisting of, resembling, or pertaining to protein.

In a more preferred embodiment of the present invention, the expression product may be a polypeptide of interest which is expressed and thus produced.

It is preferred that the expression product is biologically active.

The expression product can be the product of transcription and/or translation of a nucleotide sequence, preferably of a nucleotide sequence that is exogenously added to the host cell by means and methods commonly known in the art in the context of genetically engineering host cells. The expression product can thus be a nucleotide sequence (as such) including, for example, a ssDNA or dsDNA sequence or RNA sequence (ribozyme, antisense RNA, siRNA, iRNA, miRNA and the like), all of which are capable of being expressed in the host cell or it can be a polypeptide that is generated by way of translation of the transcribed RNA in the host cell.

A "polypeptide" includes proteins, polypeptides and fragments thereof, said fragments being preferably biologically active. The terms "polypeptide" and "protein" are used interchangeably to refer to polymers of amino acids of any length, generally more than about 10, 20 or 30 amino acids. These terms also include proteins that are post-translationally modified through reactions that include glycosylation, acetylation and phosphorylation. The term "peptide" refers to shorter stretches of amino acids, generally less than about 30 amino acids.

A polypeptide can serve as agonist or antagonist, and/or have therapeutic or diagnostic uses.

Further, a polypeptide expressed in a host cell of the present invention can be of mammalian origin although microbial and yeast products can also be produced.

Examples of mammalian polypeptides or proteins include hormones, cytokines and lymphokines, antibodies, receptors, adhesion molecules, and enzymes as well as fragments thereof. A non-exhaustive list of desired products include, e.g., human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A- or B-chain; prorelaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), growth factors including vascular endothelial growth factor (VEGF), nerve growth factor such as NGF-; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-11); des (1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha,-beta, and -gamma; colony stimulating factors (CSFs), e.g., M-CSF, GM-CSF, and G-CSF; interleukins (ILs), e.g., IL-1 to IL-10; superoxide dismutase; erythropoietin; T-cell receptors; surface membrane proteins e.g., HER2; decoy accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

Examples of bacterial polypeptides or proteins include, e.g., alkaline phosphatase and B-lactamase.

Preferred polypeptides and proteins herein are therapeutic proteins such as TGF-β, TGF-α, PDGF, EGF, FGF, IGF-I, DNase, plasminogen activators such as t-PA, clotting factors such as tissue factor and factor VIII, hormones such as relaxin and insulin, cytokines such as IFN-γ, chimeric proteins such as TNF receptor IgG immunoadhesin (TNFr-IgG) or antibodies such as anti-IgE. Preferred therapeutic proteins are those of human origin or "humanized" proteins such as humanized antibodies.

If the expression product is a polypeptide, it is preferred that said polypeptide is tagged, i.e., fused with a heterologous polypeptide which preferably allows isolation and/or purification of said expression product being a polypeptide. The heterologous polypeptide can, for example, be a histidine tag, streptavidin tag, an intein, maltose-binding protein, an IgA or IgG Fc portion, protein A or protein G.

If the expression product is a nucleotide sequence, it is preferred that it is fused with a heterologous nucleotide sequence which allos isolation and/or purification of said expression product being a nucleotide sequence. For example, the heterologous nucleotide sequence can bind to a complementary nucleotide sequence, thereby allowing isolation and/or purification of said expression product being a nucleotide sequence. "Heterologous" when used in the context of a heterologous polypeptide or nucleotide sequence means that a polypeptide or nucleotide sequence is different from the polypeptide or nucleotide sequence being the desired expression product. However, while it is different, it can nevertheless be from the same organism, but can also be from a different organism. The expression product is preferably isolated and/or purified from filtrate 2 (eluate 2).

On the other hand, the host cell may express a virus, i.e., the host cell serves as producer cell line that provides, so to say, the appropriate environment that the virus replicates and/or is propagated. Accordingly, it is a preferred embodiment of the present invention that the expression product is a virus.

Virtually, any virus can be recovered by the methods of the present invention such as dsDNA viruses (e.g. Adenoviruses, Herpesviruses, Poxviruses), ssDNA viruses (e.g. Parvoviruses), dsRNA viruses (e.g. Reoviruses), (+) ssRNA viruses (e.g. Picornaviruses, Togaviruses), (−) ssRNA (e.g. Orthomyxoviruses, Rhabdoviruses), ssRNA-RT viruses (e.g. Retroviruses) and dsDNA-RT viruses (e.g. Hepadnaviruses).

Viral replication is the term used to describe the formation of virus during the infection and propagation process in the target host cells. From the perspective of the virus, the purpose of viral replication is to allow production and survival of its kind. By generating abundant copies of its genome and packaging these copies into viruses, the virus is able to continue infecting new hosts. In the context of the present invention it is preferred that viruses produced by appropriate host cells are not or essentially not capable of exiting the host cell, for example, by way of lysis or budding.

It is preferred that the expression product, in particular, a virus is biologically active. If the expression product is a virus, in particular a Vaccinia virus, "biological activity" is defined as Vaccinia virus virions that are either 1) infectious in at least one cell type, e.g. CEFs, 2) immunogenic in humans, or 3) both infectious and immunogenic. A "biologically active" Vaccinia virus is one that is either infectious in at least one cell type, e.g. CEFs, or immunogenic in humans, or both. In a preferred embodiment, the Vaccinia virus is infectious in CEFs and is immunogenic in humans.

As mentioned before, the expression product may preferably be a virus. A "virus" includes "native" viruses and "recombinant" viruses, with "native" meaning a virus which is isolated from nature and not genetically engineered (such as a clinical isolate) or a virus which can be found in nature (i.e., naturally-occurring) or a typical, established virus strain, for example used for immunization purposes (such as an attenuated virus).

The term "recombinant virus" encompasses any virus having inserted into the viral genome a heterologous gene that is not naturally part of the viral genome. A heterologous gene can be a therapeutic gene, a gene coding for an antigen or a peptide comprising at least one epitope to induce an immune response, an antisense expression cassette or a ribozyme gene. Methods to obtain recombinant viruses are known to a person skilled in the art. The heterologous gene is preferably inserted into a non-essential region of the virus genome. In another preferred embodiment of the invention, the heterologous nucleic acid sequence is inserted at a naturally occurring deletion site of the MVA genome (disclosed in PCT/EP96/02926), more preferred in an intergenic region of the viral genome (PCT/EP03/05045). Alternatively, the heterologous nucleic acid sequence can be inserted at different loci within the poxvirus, preferably MVA genome, in particular, if two or more nucleic acid sequences are inserted (disclosed in EP 1 506 301).

As mentioned above, the term "virus" encompasses, apart from native or recombinant viruses, also attenuated viruses. The term "virus" also includes "components" of a virus. Such components embrace, for example viable (La capable of multiplication) or inactivated freshly isolated viruses, viable or inactivated recombed viruses derived from freshly isolated viruses, viable or inactivated attenuated viruses, viable or inactivated recombed viruses derived from attenuated viruses, the detached envelopes and cleavage products and aberrant forms of said envelopes of the viruses mentioned herein, individual viral polypeptides obtained by biochemical or immunochemical methods from cultures that had been infected with the viruses mentioned herein, and recombinant viral polypeptides obtained by means of prokaryotic or eukaryotic expression and at least parts of which are derived from one or more of the viral polypeptides of the viruses mentioned herein. Such components when administered to a subject induce preferably an immune response, i.e., they are immunogenic. An immune response includes a humoral and/or cellular immune response.

An "attenuated virus" is a virus that upon infection of the host organism results in a lower or even none mortality and/or morbidity compared to the non-attenuated parent virus. An example for an attenuated Vaccinia virus is strain MVA, in particular MVA-575 and MVA-BN.

In a preferred embodiment the virus is a virus of the Poxviridae, preferably a poxvirus, more preferably a fowlpox virus or Vaccinia virus, most preferably MVA. Because of the size of a virus of the Poxviridae, as explained herein, the filter unit applied in the method of the present invention has a size and/or structure which cannot exclude passing through of disrupted host cells (as characterized herein), since disrupted host cells may have a size which equals that of a virus and, thus, disrupted host cells can pass through said filter unit. However, the application of one or more of the further purification methods/steps described herein below allow the separation of said virus from disrupted host cells.

In the context of the present invention the term "poxvirus" refers to any virus belonging to the family poxviridae. The family of poxviridae can be divided into the subfamily chordopoxvirinae (vertebrate poxviruses) and entomopoxvirinae (insect poxviruses).

The chordopoxvirinae comprise several animal poxviruses (classified in different genera) of significant economical importance, such as camelpox viruses, sheeppox virus, goatpox virus or avipoxviruses, in particular fowlpoxvirus.

The virus is preferably a poxviridae of the subfamily chordopoxvirinae, more preferably of the genera orthopoxvirus, avipoxvirus, capripoxvirus and suipoxvirus. More preferably the virus is selected from the group consisting of Vaccinia virus, goat poxvirus, sheep poxvirus, canary poxvirus and fowl poxvirus.

As mentioned, more preferred is Vaccinia virus. Examples for vaccinia virus strains used in the method according to the present invention are the strains Elstree, Wyeth, Copenhagen, Temple of Heaven, NYCBH, Western Reserve. The invention is not restricted to those specifically mentioned vaccinia virus strains but may instead be used with any vaccinia virus strain. A preferred example for a Vaccinia virus strain is the modified Vaccinia virus strain Ankara (MVA). A typical MVA strain is MVA 575 that has been deposited at the European Collection of Animal Cell Cultures under the deposition number ECACC V00120707. Most preferred is MVA-BN or a derivative/variant, in particular an MVA-BN derivative/variant having the same properties, specifically the same safety profile, as the deposited MVA-BN strain. MVA-BN has been described in WO 02/42480 (PCT/EP01/13628). Said international application discloses biological assays allowing evaluating whether an MVA strain is MVA-BN or a derivative thereof and methods allowing obtaining MVA-BN or a derivative/variant. The content of this application is included in the present application by reference. MVA-BN has been deposited at the European Collection of Animal Cell Cultures with the deposition number ECACC V00083008.

When used herein in the context of MVA-BN, "a derivative" has preferably the same properties as MVA-BN, i.e., the capability of reproductive replication in chicken embryo fibroblasts (CEF), but no capability of reproductive replication in the human keratinocyte cell line HaCat, the human bone osteosarcoma cell line 143B, and the human cervix adenocarcinoma cell line HeLa. Tests and assay for these properties of MVA are described in WO 02/42480 and WO 03/048184 (incorporated by reference).

Particularly preferred polypeptides that are preferably comprised by a virus expressed (produced) by a host cell are B. anthracis protective antigen (PA), Her2-neu, PSA, PAP (also a combination thereof), HIV antigens including Nef, measles virus antigen. These polypeptides are preferably expressed by a recombinant poxvirus, preferably by MVA. Accordingly, in this particularly preferred embodiment, poxviruses are produced that are used as vaccines: PROST-VAC™, MVA-BN® PRO, MVA-BN® HER2, The MVA-BN® HIV multiantigen, MVA-BN® Measles.

The expression product recovered by the method of the present invention is an essentially cell-associated expression product. "Cell-associated" when used herein means that the expression product is preferably within or attached to a host cell including intracellularly present/expressed/produced expression products that are, for example, present in soluble form in the cytoplasm or in the form of inclusion bodies. Accordingly, the methods of the present invention allow the release of the intracellularly located expression product such as a polypeptide by collecting host cells expressing the expression product.

The term "cell-associated" when used herein also means that the expression product such as a virus is attached to cellular membranes in the cytoplasm of the host cell. For example, poxviruses, such as Vaccinia virus, are known to exist in different forms (vaccinia virus forms): As used herein "vaccinia virus forms" refer to the three different types of virions produced by infected target cells: Mature virions (MV), wrapped virions (WV), and extra-cellular virions (EV) (Moss, B. 2006, Virology, 344:48-54). The EV form comprises the two forms previously known as cell-associated enveloped virus (CEV), and extra-cellular enveloped virus (EEV) (Smith, G. L. 2002, J. Gen. Virol. 83: 2915-2931). The MV and EV forms are morphologically different since the EV form contains an additional lipoprotein envelope. Furthermore, these two forms contain different surface proteins (see Table 1 of WO 2008/138533), which are involved in the infection of the target cells by interaction with surface molecules on the target cell, such as glycosaminglycans (GAGs) (Carter, G. C. et al. 2005, J. Gen. Virol. 86: 12791290). The invention preferably involves use of the recovery of all vaccinia virus forms including the MV and WV forms of Vaccinia Virus, apart from the EV form. The MV form can, for example, be preferentially isolated by binding of the MV form to glucosamine glycans (GAG) or GAG-like molecules such as heparane sulfate or heparin.

"Essentially", when used in the context of cell-association of the expression product, means that the expression product is—because it is in the nature of an expression process—not 100% cell-associated. While a proportion of the expression product may be cell-associated, another proportion may not be cell-associated. For example, a proportion of a an expression product, such as a polypeptide, may be intracellularly, while another proportion may be extracellularly, i.e., secreted. Accordingly, the term "essentially" preferably means that the expression product is at least 50% cell-associated, more preferably at least 60% cell-associated, even more preferably at least 70% cell-associated, particularly preferred at least 80% cell-associated, even more particularly preferred at least 90% cell-associated and most particularly preferred at least 95% cell-associated. "Culturing" a host cell means that an appropriate host cell is grown under conditions that allow expression of the expression product.

It is a preferred embodiment that culturing a host cell as applied in the methods of the present invention is done as suspension culture or adherent culture or as a combination of both.

The term "cultivation of cells" or "culturing of cells" in medium (either with serum or serum free) in the context of the host cells of the present invention refers to the seeding of the cells into the culture vessel, to the growing of the cells in medium in the logarithmic phase until, in case of adherent culturing, a monolayer is formed, or, in case of a suspension culture, a sufficient cell density is established and/or to the maintenance of the cells in medium as soon as the monolayer is formed or to the maintenance of the cells in suspension, respectively. The term "cultivation of cells" or "culturing of cells" in medium also includes that all of the above mentioned steps are performed with serum free medium, so that no or essentially no animal serum products are present during the whole cultivation process of the cells. Yet, in the alternative, the above mentioned steps may also be performed with serum containing medium.

Preferably, the media used in all of the above steps may comprise a factor selected from growth factors and/or attachment factors. However, it might be sufficient to add such a factor only to the media used for the seeding of the cells and/or the growing of the cells under logarithmic conditions.

As explained below in more detail it might also be possible to cultivate cells that would normally grow as attached cells also as suspension culture cells if appropriate incubation conditions are chosen (e. g. by applying "wave" incubation). The method according to the present invention also applies for this type of incubation as a particular preferred embodiment.

The term "serum-free" medium refers to any cell culture medium that does not contain sera from animal or human origin. Suitable cell culture media are known to the person skilled in the art. These media comprise salts, vitamins, buffers, energy sources, amino acids and other substances. An example of a medium suitable for the serum free cultivation of CEF cells is medium 199 (Morgan, Morton and Parker; Proc. Soc. Exp. Bioi. Med. 1950,73, 1; obtainable inter alia from LifeTechnologies) or VP-SFM (Invitrogen Ltd.) which is preferred.

Culturing can be done in any container suitable for culturing cells, for instance in dishes, roller bottles or in bioreactors such as the WAVE™ bioreactor system, by using batch, fed-batch, continuous systems, hollow fiber, and the like. In order to achieve large scale (continuous) production of virus through cell culture it is preferred in the art to have cells capable of growing in suspension, and it is preferred to have cells capable of being cultured in the absence of animal- or human-derived serum or animal- or human-derived serum components. Suitable conditions for culturing cells are known (see e.g. Tissue Culture, Academic Press, Kruse and Paterson, editors (1973), and R. I. Freshney, Culture of animal cells: A manual of basic technique, fourth edition, Wiley-Liss Inc., 2000, ISBN 0-471-34889-9.

It is a particular preferred embodiment of the present invention that host cells expressing an expression product as described herein are cultured in suspension (suspension culture) in a non-disposable or disposable bioreactor such as preferably the WAVE™ bioreactor system.

The WAVE Bioreactor™ system consists of two components: disposable cell bags and a rocker. Culture medium and cells only contact a presterile, disposable chamber called a cellbag that is placed on a special rocking platform. The rocking motion of this platform induces waves in the culture fluid. These waves provide mixing and oxygen transfer, resulting in a perfect environment for cell growth that can easily support over $10 \times 10^6$ cells/ml. Cellbags are available from 0.1 to 500 liters of culture volume. The WAVE Bioreactor™ system provides the environment to culture host cells of the present invention under GMP-principles of aseptic processing. Disposable bioreactors such as The WAVE Bioreactor™ system offer a number of advantages including the reduction of preparation time, elimination of cleaning and sterilization time, and ease of use. Furthermore, the bioreactor requires no cleaning or sterilization, providing ease in operation and protection against cross-contamination.

If the infected cells are more or less intact adherent cells they should be harvested, i.e., removed from the culture container, before subjecting them to homogenization. Such methods are known to the person skilled in the art. Useful techniques are mechanic methods (e. g. by using a rubber cell scraper), physical methods (e. g. freezing below −15° C. and thawing the culture vessels above +15° C.) or biochemical methods (treatment with enzymes, e. g. trypsin, to detach the cells from the culture vessel). If enzymes are used for this purpose the incubation time should be controlled, since these enzymes may also damage the virus during incubation.

It is preferably envisaged that as host cells for the expression of an expression product a continuous cell culture is used. As used herein, "continuous cell culture (or immortalized cell culture)" describes cells that have been propagated in culture since the establishment of a primary culture, and they are able to grow and survive beyond the natural limit of senescence. Such surviving cells are considered as immortal. The term immortalized cells were first applied for cancer cells which were able to avoid apoptosis by expressing a telomere-lengthening enzyme. Continuous or immortalized cell lines can be created e.g. by induction of oncogenes or by loss of tumor suppressor genes.

For example, host cells for the production of a virus are cultured to increase cell and virus numbers and/or virus titers. Culturing a host cell is done to enable it to metabolize, and/or grow and/or divide and/or produce virus of interest according to the present invention. This can be accomplished by methods as such well known to persons skilled in the art, and includes but is not limited to providing nutrients for the cell, for instance in the appropriate culture media.

"Collecting" host cells includes any measure to concentrate, capture, harvest and/or enrich host cells expressing (producing) the expression product of the present invention in/on a separation or filter unit. For example, it is envisaged that host cells as applied in the present invention may be enriched before they are collected and/or are concentrated before they are collected and/or are captured before they are collected. Enriching may, for example, be achieved by batch centrifugation, flow through centrifugation and/or tangential flow filtration.

It is preferred that host cells are collected in bulk (or in mass), i.e., bulk collection (mass collection) is performed. This is a difference to the collection of host cells by way of collecting them as entire colonies such as yeast or bacterial colonies on a membrane.

For example, when being collected, culture medium containing suspended host cells is transferred from the container to a filter unit in, preferably in an aseptic manner. Preferably, culture medium containing the host cells is pumped from the container to the filter unit and is then allowed to pass through the filter unit, preferably in an aseptic manner, thereby culture medium passes through the filter unit, while host cells are retained. In fact, it is a preferred embodiment of the present invention that culture medium containing host cells cultured as described herein is pumped to/through a filter unit, thereby host cells are retained in/on a filter unit as bulk and thus concomitantly separated from the culture medium in that said host cells are retained on/in said filter unit and culture medium is allowed to pass through the filter unit. In order to transfer host cells to a filter unit, the host cells are in suspension—either the host cells are as such in suspension or, if adherently grown, are brought in suspension as described herein. The filter unit is preferably rinsed (preferably with a suitable solution, preferably with a buffer) prior to receiving the host cells suspended in the culture medium.

Cell disruption in/on the filter unit used to collect host cells expressing the expression product is the decisive feature that distinguishes the methods of the present invention from the thus far applied methods for recovering an essentially cell-associated expression product from host cells, in particular a virus being the expression product. Specifically, the prior art did, to the best of applicant's knowledge, neither recognize nor suggest that host cells can be disrupted (preferably lysed) in/on a filter unit used to collect said host cells. Thus far, host cells were, for example, disrupted by sonication, freeze-thawing, high-pressure homogenization, mechanical grinding, etc., but not in/on the filter unit. Rather, cell disruption in the prior art takes place during culturing said host cells or after cells were harvested, for example, by flow-through ultrasonication or high pressure homogenization.

Moreover, filter units were commonly applied only in further down-stream processing after the cells were disrupted in order to clarify the homogenate/lysate. However, even for the present inventors the success they had in disrupting host cells expressing the desired expression product in/on the filter unit used to collect said host cells came as a surprise. The quality of disrupting host cells in accordance with the teaching of the present invention is believed to be as good as the quality of prior art methods, perhaps it may even be improved. For example, the recovery of poxviruses revealed a comparable titer combined with a significantly reduced impurity profile, when compared to alternative manufacturing processes using ultrasonication to homogenize host cells expressing poxvirus in cell culture. On the basis of the teaching of the prior art, one could have reasonably assumed that disruption of host cells in/on a filter unit would not efficiently occur, since cells are stacked and/or arranged in tiers which might render at least those cells inaccessible to cell disruption (preferably by lysis) that are covered/surrounded in a bulk by other cells, for example, physical shielding and/or protective effects at the surface of the collected host cells could have occurred. However, despite the reservations that one would have had in disrupting (preferably lysing) host cells, the present inventors surprisingly found that the disruption of host cells in bulk is as efficiently as a known and commonly applied method for disrupting host cells in order to recover their expression product (see Example 3).

Any filter unit can be applied as long as its structure and/or pore size is preferably (i) capable of retaining the (intact) host cells applied in the methods of the present invention and (ii) allows elution of the expression product from the filter unit after disruption of the host cells expressing said expression product. As described above, in some preferred embodiments disrupted host cells can essentially not pass through said filter unit, while the expression product can pass through. This property of the filter unit is dependent on the pore size and/or structure of said filter unit in relation to the size of the expression product.

However, as also described above, in other preferred embodiments, disrupted host cells can, in addition to the expression product, also pass through said filter unit. This property of the filter unit is again dependent on the pore size and/or structure of said filter unit, since the pore size of said filter unit may have a size which allows the expression product to pass through. However, that size may also allow disrupted host cells to pass through said filter unit.

Thus, in sum, the filter unit may in some preferred embodiments, because of its (small) pore size and/or structure already allows a separation of disrupted host cells from their expression product, while in other preferred embodiments the filter unit, because of its (large) pore size and/or structure, cannot efficiently retain disrupted host cells which thus pass through. If so, separation of the disrupted host cells and their expression product is achieved by one or more of the further purification steps provided by the present invention (described herein below).

The filter unit applied in the methods of the present invention is particularly preferable a filter unit applicable in depth filtration, i.e., it is a depth filter unit.

As regards the expression product, it is envisaged that all expression product can pass through the filter unit. However, it is believed that 1, 2, 3, 4, 5, 10 or 20%, but not more of the total expected expression product may not pass through the filter unit.

However, as described herein it may occur that disrupted host cells pass through, if the pore size and/or structure of said filter unit have to be adjusted to the size of the expression product. In essence, the choice of the filter unit is dictated by the "size" and structure of the host cell and the size and structure of the expression product of said host cell.

The filter unit applied in the methods of the present invention is preferably capable of retaining host cells (retenate), thereby allowing the separation of host cells from the cell culture medium (sometimes referred to herein as "filtrate 1" or "eluate 1"). During that step, potential impurities are deemed to be separated from said host cells, since the filter unit allows flow through of culture medium containing, for example, media components, supplements, growth factors, energy sources, vitamins, impurities or secreted expression product or otherwise released expression product because of the pore size and/or the structure of said filter unit. Afterwards, host cells are disrupted in/on said filter unit, thereby the expression product is released and can be recovered (sometimes referred to herein as "filtrate 2" or "eluate 2").

In some preferred embodiments, said filtrate 2 (eluate 2) is, because of the pore size and/or structure of the filter unit essentially free of disrupted host cells, in particular essentially free of cell membranes, cell fragments and the like.

In other preferred embodiments, said filtrate 2 (eluate 2) may contain, because of the pore size and/or structure of the filter unit, disrupted host cells.

In a particular preferred embodiment, the cultured host cells expressing the expression product of the present invention are collected by way of pumping the culture medium with the host cells being in suspension through a filter unit. For that particular preferred embodiment, aseptic connection of filter units is applied in order to meet principles of aseptic processing.

Even if some expression product which, as described above, may not 100% be cell-associated, but to a certain extent secreted, would be present in the cell culture medium that is separated from the host cells (i.e., the filtrate 1), said expression product could be retained on a further filter unit coupled in series to the first (or subsequent filter unit coupled in series to said first filter unit), provided that said further filter unit has a pore size and/or structure suitable to retain said expression product. Accordingly, with this embodiment, also potentially secreted or essentially secreted expression products (or, so to say, the amount of a cell-associated expression product that is, as described above, not 100% cell-associated) can be recovered from a host cell expressing said expression product.

The filter unit is generally to be understood as a "separation" unit, i.e., "separation" and "filter" (unit) are used interchangeably. In particular, the filter unit separates host cells from cell culture medium. The filter/separation unit preferably applied in the methods of the present invention is a fleece, holofiber (such as glass fiber) or membrane. In a particular preferred embodiment, the filter unit is composed of polypropylene.

The hollow fiber modules consist of an array of self-supporting fibers with a dense skin layer that give the membranes its permselectivity. Fiber diameters range from 0.5 mm-3 mm. An advantage of hollow fiber modules is the availability of filters from small membrane areas (ca. 16 cm$^2$) to very large membrane areas (ca. 28 m$^2$) allowing linear and simple scale-up.

In some embodiments, there may be one filter unit, while in other embodiments, there may be two or more filter units coupled in series, whereby cell disruption takes place in/on the first filter and each subsequent filter. Alternatively and/or additionally filter units may be used in parallel.

In the context of the filter unit, it is said that cell disruption takes place "in/on" said filer unit. This is so because, some filter units are built such that cells adhere to membranes of said filter unit so that disruption takes place on the membrane surface of said filter unit, while other filter units are built such that cells do not adhere to the membranes of said filter unit and cell disruption takes place within said filter unit, i.e., host cells are retained in, for example, a three-dimensional structure (such as a molecular sieve) and thus, are "in" said filter unit, but can essentially not pass through said filter unit and can, thus, generally not be found in eluate 1. After their disruption in/on said filter unit, disrupted host cells may pass through said filter or may even be retained in/on said filter unit (dependent on the pore size and/or structure of said filter unit).

However, since the methods of the present invention are preferably for the recovery of an expression product being a virus, preferably a virus selected from the group consisting of fowlpox virus, vaccinia virus and modified vaccinia virus Ankara (MVA), a filter unit is required with a pore size and/or structure that allows passing through of said virus. Because of its pore size and/or structure such a filter unit may also allow passing through of disrupted host cells, i.e., it cannot exclude passing through of disrupted host cells. Yet, disrupted host cells can readily be separated from the desired expression product by one or more of the purification steps/methods described herein. In that embodiment, the filter unit is, so to say, a host cell collector which allows disruption of host cells in bulk in a closed process, thereby the released expression product is concentrated in the filtrate (i.e., in filtrate 2 or eluate 2), since, in case of the preferred method for disrupting host cells (i.e., lysis) the volume of filtrate 2 is dependent on the amount of solution used to lyse the host cells and/or used to elute the expression product from said filter unit.

In general, when the host cells are in/on said filter unit, cell disruption as described herein takes place.

Preferably, cell disruption is done by lysis, preferably with a hypotonic solution, preferably a hypotonic lysis buffer. Accordingly, in a particular preferred embodiment, host cells collected in/on said filter unit are lysed by way of a hypotonic solution (preferably a buffer) and the released expression product is eluted by way of flow through of the hypotonic solution. Elution takes place because of the size and/or structure of said filter unit that allows the expression product to pass through (eluate or filtrate 2), i.e., the eluate is capable to pass the filter unit and can thus be recovered.

The recovered expression product may then be subjected to further down-stream processing as described herein below.

The filter unit applied in the methods of the present invention has preferably a pore size of less than about 10 μm (such as Polypropylen fleece filters), more preferably a pore size between about 1.2 μm and about 5 μm; and even more preferably it has a pore size of about 3 μm.

In a particularly preferred embodiment, the host cells collected in/on the filter unit are disrupted by lysis through a hypotonic buffer, preferably by lysis with a 1 mM Tris buffer pH 9.0. This embodiment is preferably applied for the expression of poxviruses in suitable host cells, preferably in CEF cells.

Cell disruption includes rupturing of cell membranes or cell wall and release of the cytoplasm from the cell.

Lysis can be either hypertonic or hypotonic lysis, with hypotonic lysis being preferred, more preferably with a hypotonic lysis solution. Said solution is preferably a buffer (hypotonic or hypertonic lysis buffer, with hypotonic lysis buffer being preferred). Though less preferred, hypertonic lysis can be achieved with any lysis solution, preferably a buffer that has a salt concentration higher than interior of the host cell to be lysed, i.e., the hypertonic lysis buffer has an osmolarity higher than the host cell to be lysed.

Any hypotonic lysis buffer can be applied as long as its salt concentration is lower than the interior of the host cell to be lysed, i.e., the hyptonioc lysis buffer has an osmolarity lower than the host cell to be lysed.

Particularly preferred, lysis is achieved by a hypotonic lysis buffer selected from the group consisting of 1 mM Tris pH 9.0. Similarly, 1-10 mM PBS buffer at various pH values could also be used.

Though less preferred, lysis can also be achieved by detergent lysis.

Detergents, as used herein, can include anionic, cationic, zwitterionic, and nonionic detergents. Exemplary detergents include but are not limited to taurocholate, deoxycholate, taurodeoxycholate, cetylpyridium, benzalkonium chloride, ZWITTERGENT-3-14®, CHAPS (3-[3-Cholamidopropyl) dimethylammoniol]-1-propanesulfonate hydrate, Aldrich), Big CHAP, Deoxy Big CHAP, Triton X-100®, Triton X-114®, C12E8, Octyl-B-D-Glucopyranoside, PLURONIC-F68®, TWEEN-20®, TWEEN-80® (CAL-BIOCHEM® Biochemicals), deoxycholate, Triton X-100, Thesit®, NP-40®, Brij-58®, octyl glucoside, and the like. It is clear to the person skilled in the art that the concentration of the detergent may be varied, for instance within the range of about 0.1%-5% (w/w). In certain embodiments the detergent is present in the lysis solution at a concentration of about 1% (w/w).

Lysis may also be achieved by enzymatic processes, sonification (ultrasound), high pressure homogenization, high pressure extrusion, french pressing, freeze-thawing, solid shear, enzymatically, or by lysis, combinations of these techniques; with lysis being preferred.

If the host cells expresses (produces) a virus, the success of cell disruption (preferably lysis) may preferably be checked by determination of the virus titer (equivalent to the number of infectious virus particles, measured either in tissue culture infectious dose ($TCID_{50}$), or plaque forming units (pfu)) of the starting material as defined above and of the material obtained after cell disruption. In other words the virus titer is determined before and after the cell disruption. The starting material comprises more or less intact cells and a rather high percentage of large aggregates comprising virus particles bound to cellular membranes. If such a material is used for the determination of the viral titer, the obtained titer is lower than the actual number of infectious particles. This is due to the fact that the test systems used for the determination of the viral titer are usually cell culture systems in which the number of infected cells or the number of plaques is counted. Such a system can not distinguish between a positive result that is due to the infection of a cell by just one virus particle and the infection of cells e.g. by a large aggregate of viruses bound to cellular membranes. It is believed that after the cell disruption the viruses become detached from the cellular membranes and/or the size of cell membrane-virus aggregates is significantly reduced, which leads to a larger number of smaller aggregates. If this material is used for the determination of the titer the obtained results are higher, even if the actual amount of infectious virus particles has not changed. Thus, the success of cell disruption is preferably reflected by at least an equal or higher $TCID_{50}$/ml. "TCID" is the abbreviation of "tissue culture infectious dose" of the disrupted cells (preferably a lysate thereof) or PFU/ml compared to the starting material. Alternatively, the quality and the success of the cell disruption can be determined by electron microscopy.

If the host cell expresses a polypeptide, the success of cell disruption may preferably determined by quantitating the amount of the expression product that is released from the host cells by means and methods commonly known in the art, such as ELISA and the like.

The separation step of the method of the present invention allows in some embodiments the separation of disrupted host cells from the expression product expressed by said host cells. Hence, the separation step is equal to an elution step. Nevertheless, an additional elution step may be applied. However, in order to allow separation of disrupted host cells from the expression product, the pore size and/or structure of the filter unit applied in the methods of the present invention must be chosen accordingly as explained herein.

In other preferred embodiments, the separation step of the method of the present invention takes place after, in particular the expression product, and the disrupted host cells passed through the filter unit. Preferably, the expression product is eluted after host cells were disrupted. Elution is concomitantly achieved while host cells are disrupted, for example, preferably through lysis by a solution, and/or is achieved when eluting said expression product from the filter unit. In view of the fact that in these other preferred embodiments, a filter unit is applied with a pore size and/or structure that cannot exclude that disrupted host cells also pass through the filter unit, the separation step does essentially not occur in/on said filter unit, but in filtrate 2 (eluate 2). "Essentially not" means that it is not excluded that disrupted host cells may be retained in/on said filter unit.

Though less preferred it is nevertheless envisaged that the expression product and the host cells are retained in/on the filter unit or that the expression product is retained in/on the filter unit such that, after the host cells are removed, the expression product can be recovered. For example, the expression product may (reversibly) bind to the filter unit, for example, by a receptor-ligand interaction or by affinity binding, for example, by flushing or a washing step. Of course, the filter unit has to be prepared accordingly. Affinity binding may preferably be used to retain poxviruses including preferably fowlpoxvirus, Vaccinia, more preferably MVA. It is known that poxviruses can bind to glucosamine glycane (GAG) or a GAG-like ligand including, for example, carbohydrates with a negatively charged sulfate group, heparan sulfate or heparin (see WO 2008/138533).

Elution of bound poxviruses can be achieved with an excess of GAG or a GAG-like ligand or part thereof.

Also, though less preferred, the separation step may allow the host cells after their disruption to pass through the filter unit, while the expression product is retained in/on said filter unit. As described above, this less preferred separation may be achieved through affinity- or pseudo affinity binding of the expression product to the filter unit, while disrupted host cell will pass through.

In a preferred embodiment of the methods of the present invention, a nuclease is added to remove contaminants, i.e., mostly host cell, nucleic acids. Exemplary nucleases suitable for use in the present invention include Benzonase®, Pulmozyme®, or any other DNase and/or RNase commonly used withing the art. In preferred embodiments of the invention, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950).

The concentration in which the nuclease is employed is preferably within the range of 1-100 units/ml.

According to the invention, the nuclease is employed before or after the cells are lysed. It may be added just seconds prior to (or virtually concomitant with) or after the lysis step, but preferably the nuclease is added after the lysis step.

It is preferred that the host cell applied in the methods of the present invention are eukaryotic cells including mammalian and non-mammalian cells as further specified herein. More preferably, the host cells are vertebrate cells or insect cells, preferably avain cells.

A "host cell" refers to a cell which is capable of expressing (producing) the expression product. Said host cell is applied in the methods of the present invention. For that purpose, if the host cell is to express a polynucleotide or a polypeptide, a foreign nucleotide sequence expressing the expression product is introduced in the host cell.

By "foreign" it is meant that the nucleotide sequence and/or the encoded polypeptide is either heterologous with respect to the host, this means derived from a cell or organism with a different genomic background, or is homologous with respect to the host but located in a different genomic environment than the naturally occurring counterpart of said nucleotide sequence. This means that, if the nucleotide sequence is homologous with respect to the host, it is not located in its natural location in the genome of said host, in particular it is surrounded by different genes. In this case the nucleotide sequence may be either under the control of its own promoter or under the control of a heterologous promoter.

Yet, if the host cell is to express (produce) a virus, it is preferred that it is infected with said virus in order to propagate and/or replicate the virus. Infecting of host cells can for instance simply be accomplished by exposing the virus to the appropriate host cell under physiological conditions, permitting uptake of the virus. For certain viruses it is not even necessary to start with virus per se, as nucleic acid sequences may be used to reconstitute the virus in the cultured cells.

The term "infected cells" used to define the starting material for the recovery of an expression product refers to intact cells infected with the respective virus, to parts and fragments of infected cells to which the respective virus is attached or to a mixture of intact cells and lysed/disrupted cells. Examples for a part or a fragment of infected cells are cell membranes of disrupted/lysed cells to which the respective virus is attached. The starting material may also contain free virus particles that are neither attached to cellular membrane nor located intracellularly.

Preferably, the host cell includes both prokaryotic cells used for propagation of the construct to prepare plasmid stocks, and eukaryotic cells for expression of the expression product. More preferably, the host cell applied in the methods of the present invention are vertebrate cells including mammalian, avian, amphibian and fish cells and insect cells. Also included by the term "host cells" are eukaryotic cells. Typically, eukaryotic cells are mammalian cells, avian cells or insect cells. Furthermore, yeast and fungal cells are included by the term "host cell". Avian cells such as chicken embryonic fibroblast cells (CEF cells) are most preferred for the expression of a poxvirus, while mammalian, insect and yeast cells are preferably used for the expression of a protein as described herein.

For the expression of a virus, any suitable host cell can be used, with a host cell that is a packaging cell line being preferred for the expression of adenoviruses and retroviruses. A packaging cell lines provides elements such as factors required for viral replication and coat proteins, etc. which the virus requires to replicate and finish its life cycle.

Preferably, for the expression of viruses, in particular, adenoviruses and retroviruses as expression products the term "cell" or "packaging cell" refers to a cell which can be infected by the virus, preferably adenoviruses and retroviruses to be expressed (produced). The cell or packaging cell can be a primary cell, a recombinant cell and/or a cell line. For example, a recombinant cell which contains the elements necessary for the production of a recombinant virus which are lacking in a recombinant viral vector can be used.

The term "infection" refers to the transfer of the viral nucleic acid to a cell, wherein the viral nucleic acid is replicated, viral proteins are synthesized, or new viral particles assembled. In one preferred embodiment of the invention, the cell is an immortal avian cell. In another preferred embodiment of the invention, the cell is a DF1 cell (U.S. Pat. No. 5,879,924), which is a spontaneously immortalized chicken cell line derived from 10 day old East Lansing Line (ELL-0) eggs.

Immortal avian cell can be derived from embryonic stem cells by progressive severance from growth factors and feeder layer, thus maintaining growth features and infinite lifespan characteristic of undifferentiated stem). For example, the Ebx chicken cell line (WO 2005/007840) has been obtained by this process. Other examples are the AGE1.CR or EB66 cell line.

According to a preferred embodiment, a duck embryo permanent cell line can also be used. For example, the cell line, designated as December 99 (Ivanov et al. Experimental Pathology And Parasitology, 4/2000 Bulgarian Academy of Sciences) has been cultured over 140 consecutive passages and it is not tumorogenic for birds. The December 99 cell line is a standard cell culture system that has been used for research and can be applied for the needs of biotechnology.

As mentioned above, CEF cells are preferably used for the expression of a poxvirus as an expression product. The preparation and use of CEF for the production of viruses are well known to the one skilled in the art. Briefly, CEF are preferably extracted from Specific Pathogen Free (SPF) eggs. SPF eggs are commercially available, for example from Charles River Laboratories (Wilmington, Mass., USA). Said eggs are preferably more than 9 days old, more preferably between, 10 and 14 days old and even more preferably are 12 days old.

Before the extraction of the embryo, the egg is preferably disinfected. Many methods and products dedicated to the disinfection of eggs are available in the prior art. For example, incubation in a formol solution (e.g. 2% formol, 1 min.) followed by a rinsing in 70% ethanol can be done.

The cells of the embryos are then dissociated and purified. According to a preferred embodiment of the invention, the cells are subjected to an enzymatic digestion step that allows the destruction of the intercellular matrix. For this purpose, the use of enzyme able to digest the intercellular matrix is particularly useful. Such enzyme can be selected from the group comprising but not limited to Trypsin, Collagenase, Pronase, Dispase, Hyaluronidase and Neuraminidase. This enzyme can be used alone or in combination. In a particularly preferred embodiment of the invention dispase and Trypsin (e.g. TrypLE select from Gibco™) are used in combination. The one skilled in the art is able to determine the enzyme concentration, the temperature and the length of incubation allowing an efficient separation of the cells.

A eukaryotic host cell that may be applied in the methods of the present invention may be a mammalian cell, an avian cell, an amphibian cell, a fish cell, an insect cell, a fungal cell, a plant cell or a bacterial cell (e.g., E coli strains HB101, DH5a, XL1 Blue, Y1090 and JM101). Examples of eukaryotic host cells include, but are not limited to, yeast, e.g., Saccharomyces cerevisiae, Schizosaccharomyces pombe, Kluyveromyces lactis or Pichia pastoris cells, cell lines of human, bovine, porcine, monkey, avian and rodent origin, as well as insect cells, including but not limited to, Spodoptera frugiperda insect cells and Drosophila-derived insect cells as well as zebra fish cells. Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26), MRC-5 (ATCC CCL 171) and PER-C6.

In a particular preferred embodiment of the present invention, the host cell is an avian cell. The term "avian" as used herein is intended to refer to any species, subspecies or race of organism of the taxonomic class "ava", such as, but not limited to, such organisms as chicken, turkey, duck, goose, quails, pheasants, parrots, finches, hawks, crows, ostrich, emu and cassowary. The term includes the various strains of Gallus gallus, or chickens (for example White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred. In a most particular preferred embodiment, the avian cell of the present invention is a chicken cell, specifically a chicken embryo fibroblast (CEF) cell.

It is envisaged that the method according to the invention is performed, while it is preferably essentially free from animal products (except for the host cell and supplements added to culture medium). Accordingly, the enzyme(s) used for the preparation of CEF is (are) preferably of recombinant origin. However, it is also preferred that the enzyme is porcine trypsin. As used herein, "animal products" means any compound or collection of compounds that was produced in or by an animal cell in a living organism. However, it is also contemplated herein that the method according to the invention is preferably performed in the presence of animal products.

For example, where the poxvirus to produce is MVA, the virus is introduced in the cell culture container at a MOI which is preferably comprised between 0.001 and 0.1, more preferably between 0.03 and 0.07 and even more preferably about 0.05.

According to a preferred embodiment of the invention, the host cells, in particular mammalian and avian cells are cultivated at a temperature of about 37° C. or at a temperature lower than 37° C., preferably between 30° C. and 36.5° C. or between about 32° C. and about 36° C., more preferably between 33° C. and 35° C., most preferably at 34° C.

It is a preferred embodiment of the present invention that the expression product once released (filtrate 2 or eluate 2) from the host cell by cell disruption in/on a filter unit is optionally further purified, i.e., clarified.

Purification may preferably achieved by a chromatography step selected from one or more members of the group consisting of anion exchange chromatography, size exclusion chromatography, hydrophobic interaction chromatography, pseudo-affinity chromatography, or a combination thereof.

In the alternative and/or addition to the purification by way of chromatography, preferably a clarification step can be performed. A clarification step is preferably performed when the expression product of a host cell of the present invention is a virus. Clarification allows, inter alia, removal of any cellular debris, if present. Clarification may be done by a filtration step, preferably by a depth filtration step to remove cell debris and other impurities.

Suitable filters may utilize cellulose filters, regenerated cellulose fibers, cellulose fibers combined with inorganic filter aids (e.g. diatomaceous earth, perlite, fumed silica), cellulose filters combined with inorganic filter aids and organic resins, or any combination thereof, and polymeric filters (examples include but are not limited to nylon, polypropylene, polyethersulfone) to achieve effective removal and acceptable recoveries. In general, a multiple stage process is preferable but not required. The optimal combination may be a function of the precipitate size distribution as well as other variables. In addition, single stage operations employing a relatively tight filter or centrifugation may also be used for clarification. More generally, any clarification approach including dead-end filtration, microfiltration, centrifugation, or body feed of filter aids (e.g. diatomaceous earth) in combination with dead-end or depth filtration, which provides a filtrate of suitable clarity to not foul the membrane and/or resins in the subsequent steps, will be acceptable to use in the clarification step of the present invention.

As mentioned above, in a preferred embodiment, depth filtration is performed. Also, membrane filtration such as microfiltration can be used. Microfiltration is a pressure driven membrane process that concentrates and purifies large molecules. More specifically, a solution is passed through a semi-permeable membrane whose pore sizes have been chosen to reject the large particles (viruses) in the retentate, and allow the small molecules (e.g. proteins) to pass through the membrane into the permeate. Microfiltration reduces the volume of the extraction solution.

According to a preferred embodiment of the invention, the microfiltration step is followed by a diafiltration step. These two steps can advantageously be done with the same filtration membranes. Diafiltration is an improvement of microfiltration and involves diluting the retentate with a solution to effect a reduction in the concentration of the impurities in the retentate. The dilution of the retentate allows washing out more of the impurities from the retentate. It is understood that the diafiltration may be carried out in a batch mode, semi-continuous mode, or a continuous mode. The diafiltration step can be advantageously used to change the buffer in which the virus is comprised. For example, it can be useful to exchange the buffer used in the lysis process against a buffer used for further downstream processing such as for Benzonase treatment.

Commercially available products useful in this regard are for instance mentioned in WO 03/097797, p. 20-21. Membranes that can be used may be composed of different materials, may differ in pore size, and may be used in combinations. They can be commercially obtained from several vendors.

In certain embodiments of the invention, the virus suspension is subjected to ultrafiltration/diafiltration at least once during the process, e.g. for concentrating the virus and/or buffer exchange, and/or for concentration and diafiltration of the clarified harvest. The process used to concentrate the virus according to the method of the present invention can include any filtration process (e.g., ultrafiltration (UF)) where the concentration of virus is increased by forcing diluent to be passed through a filter in such a manner that the diluent is removed from the virus preparation whereas the virus is unable to pass through the filter and thereby remains, in concentrated form, in the virus preparation. UF is described in detail in, e.g., Microfiltration and Ultrafiltration: Principles and Applications, L. Zeman and A. Zydney (Marcel Dekker, Inc., New York, N.Y., 1996).

Diafiltration (DF), or buffer exchange, using ultrafilters is an ideal way for removal and exchange of salts, sugars, non-aqueous solvents separation of free from bound species, removal of material of low molecular weight, or rapid change of ionic and/or pH environments. Microsolutes are removed most efficiently by adding solvent to the solution being ultrafiltered at a rate equal to the UF rate.

UF/DF can be used to concentrate and/or buffer exchange the suspensions containing the expression product according to the present invention in different stadia of the purification process, e. g. the lysate and/or further purified virus suspensions such as those that have undergone chromatography.

In the alternative to any of the afore mentioned methods for clarifying (purifying), in particular poxviruses, in particular selected from the group consisting of fowlpoxvirus, vaccinia virus and, more preferably, modified vaccinia virus Ankara, MVA, can be purified by the means and methods described in WO 03/138533. Briefly, poxviruses can be purified because of their capability to bind to glucosamine glycans (GAG), GAG-like molecules, hydrophobic molecules and/or to ligands comprising one or more negatively charged sulphate groups such as sulphated reinforced cellulose. For example, the specific morphological form called IMV (intracellular mature virus of vaccinia virus (including MVA) is assumed to bind, in particular, to GAG and/or GAG-like molecules and can thus be purified, since other morphological forms of vaccinia virus such as EEV are believed to not bind to GAG and/or GAG-like molecules.

According to a preferred embodiment, the process according to the invention further comprises a concentration step. More preferably, said concentration step further allows the elimination of the proteins present in the mixture obtained from the previously described steps. According to a more preferred embodiment of the invention, said concentration step is a microfiltration step.

In a second aspect, the present invention relates to the use of a filter unit characterized in that said filter unit is (i) suitable to retain a host cell; and (ii) suitable for elution of said expression product from the filter unit after cell disruption in/on said filter unit for recovering said expression product from said host cell in an aseptic process.

Preferably, said expression product recovered in the above use is a virus, preferably a poxvirus, more preferably a virus selected from the group consisting of fowlpox virus, vaccinia virus and modified vaccinia virus Ankara (MVA).

All embodiments described in the context of the methods of the present invention are equally applicable to the second aspect of the present invention, mutatis mutandis.

That being said, in the context of the uses of the present invention the following are preferred embodiments:

It is preferred that the filter unit is suitable to separate said host cell from cell culture medium.

It is furthermore preferred that the filter unit is suitable to allow disruption of said host cells in/on said filter unit.

It is also preferred that the filter unit which is suitable for elution of said expression product from the filter unit after cell disruption in/on said filter unit is suitable to separate an expression product from said host cell after cell disruption in/on said filter unit.

It is also preferred that the filter unit which is suitable for elution of said expression product from the filter unit after cell disruption in/on said filter unit is suitable to allow passing through of and/or eluting the expression product from said host cell after cell disruption in/on said filter unit.

It is furthermore preferred that the filter unit is further suitable to allow passing through of a disrupted host cell.

It is a preferred that the filter unit which is suitable for elution of said expression product from the filter unit after cell disruption in/on said filter unit is suitable to retain said disrupted host cell, thereby allowing passing through of and/or eluting said expression product.

It is another preferred embodiment that the filter unit which is suitable for elution of said expression product from the filter unit after cell disruption in/on said filter unit is suitable to retain said expression product, thereby allowing passing through of and/or eluting said disrupted host cell.

It is alternatively preferred that the filter unit is suitable to separate the expression product from said host cell, thereby retaining said disrupted host cell and said expression product and allowing passing through of and/or eluting the expression product.

It is also alternatively preferred that the filter unit is suitable to separate the expression product from said host cell, thereby retaining said disrupted host cell and said expression product and allowing passing through of and/or eluting the expression product and/or the disrupted host cell.

In a third aspect, the present invention provides a system for recovering an expression product from a host cell in an aseptic manufacturing process comprising
(a) a container suitable to grow said host cell;
(b) a filter unit characterized in that said filter unit is
  (i) suitable to retain the host cell; thereby separating them from the cell culture medium, and
  (ii) suitable for elution of said expression product from the filter unit after cell disruption in/on said filter; and
(c) optionally a lysis solution for lysing said host cell; and
(d) optionally culture medium for growing said host cell.

Preferably, said expression product recovered in the above system is a virus, preferably a poxvirus, more preferably a virus selected from the group consisting of fowlpox virus, vaccinia virus and modified vaccinia virus Ankara (MVA).

All embodiments described in the context of the methods and/or uses of the present invention are equally applicable to the third aspect of the present invention, mutatis mutandis.

In a fourth aspect, the present invention provides an expression product obtainable by the methods of the present invention. Though less preferred, said expression product might contain remnants of the host cell such as cell debris, proteins or DNA. Such remnants might be present in a preparation comprising said expression product in trace amounts such as 5, 4, 3, 2, or 1% (v/v). Also, said preparation might additionally comprise components of a virus as described herein. Preferred components are detached envelopes, cleavage products of viral envelopes or aberrant forms of said envelopes of the viruses.

If the expression product is a virus, the thus obtained virus is optionally freeze-dried. Methods of freeze-drying are known to the person skilled in the art (Day J. and McLellan M., Methods in Molecular Biology (1995), 38, Humana Press, "Cryopreservation and freeze-drying protocols").

The present invention also relates to compositions comprising an expression product obtainable by the methods of the present invention.

The present invention also relates to pharmaceutical composition comprising the expression product obtainable by the methods of the present invention. As used herein, "pharmaceutical composition" refers to a composition comprising a pharmaceutically acceptable carrier. Such a carrier is preferably isotonic, hypotonic or weakly hypertonic and has a relatively low ionic strength, such as for example a sucrose solution. Moreover, such a carrier may contain any solvent, or aqueous or partially aqueous liquid such as nonpyrogenic sterile water. The pH of the pharmaceutical composition is, in addition, adjusted and buffered so as to meet the requirements of use in vivo. The pharmaceutical composition may also include a pharmaceutically acceptable diluent, adjuvant or excipient, as well as solubilizing, stabilizing and preserving agents. For injectable administration, a formulation in aqueous, nonaqueous or isotonic solution is preferred. It may be provided in a single dose or in a multidose in liquid or dry (powder, lyophilisate and the like) form which can be reconstituted at the time of use with an appropriate diluent.

Also, as mentioned above the present invention relates to a method for the production of a pharmaceutical composition comprising the steps of the method of the present invention (such as that of claim 1) and further comprising a step of admixing/formulating the expression product recovered by said method with a pharmaceutically acceptable carrier.

The present invention can be summarized by way of the following items as follows:

1. A method for recovering an essentially cell-associated expression product from a host cell comprising
(a) culturing said host cell under conditions that allow expression of said expression product;
(b) collecting said host cell in/on a filter unit;
(c) disrupting said host cell in/on the filter unit; and
(d) separating said expression product from said disrupted host cell.

2. The method of item 1, wherein said filter unit is suitable to retain said host cell, whereby said host cell is separated from cell culture medium.

3. The method of item 1 or 2, wherein the filter unit is suitable to allow disruption of said host cells in/on said filter unit.

4. The method of any one of items 1-3, wherein said filter unit is suitable to allow passing through of and/or eluting the expression product from said host cell after cell disruption in/on said filter unit.

5. The method of item 4, wherein the filter unit is further suitable to allow passing through of a disrupted host cell.

6. The method of any one of items 1-3, wherein said filter unit is suitable to separate the expression product from said host cell, thereby retaining said disrupted host cell and allowing passing through of and/or eluting of said expression product.

7. The method of any one of items 1-3, wherein said filter unit is suitable to separate the expression product from said host cell, thereby retaining said expression product and allowing passing through of and/or eluting the disrupted host cell.

8. The method of any one of items 1-3, wherein said filter unit is suitable to separate the expression product from said host cell, thereby retaining said expression product and said disrupted host cell and allowing passing through of and/or eluting the expression product and/or the disrupted host cell.

9. Use of a filter unit characterized in that said filter unit is
(i) suitable to retain a host cell which expresses an expression product; and
(ii) suitable for elution of said expression product from the filter unit after cell disruption in/on said filter unit for recovering said expression product from said host cell.

10. A system for recovering an expression product from a host cell comprising
(a) a container suitable to grow said host cell;
(b) a filter unit characterized in that said filter unit is
(i) suitable to retain the host cell; and
(ii) suitable for elution of said expression product from the filter unit after cell disruption in/on said filter;
(c) optionally a lysis solution for lysing said host cell; and
(d) optionally culture medium for growing said host cell.

11. The use of the filter unit of item 9 or the system of item 10, wherein the filter unit is suitable to separate said host cell from cell culture medium.

12. The use of the filter unit of item 9 or 11 or the system of item 10 or 11, wherein the filter unit is suitable to allow disruption of said host cells in/on said filter unit.

13. The use of the filter unit of any one of items 9, 11 and 12 or the system of any one of items 10-12, wherein the filter unit which is suitable for elution of said expression product from the filter unit after cell disruption in/on said filter unit is suitable to separate an expression product from said host cell after cell disruption in/on said filter unit.

14. The use of the filter unit of any one of items 9, 11 and 12 or the system of any one of items 10-12, wherein said filter unit which is suitable for elution of said expression product from the filter unit after cell disruption in/on said filter unit is suitable to allow passing through of and/or eluting the expression product from said host cell after cell disruption in/on said filter unit.

15. The use of the filter unit or the system of item 14, wherein the filter unit is further suitable to allow passing through of a disrupted host cell.

16. The use of the filter unit of any one of items 9 and 11-13 or the system of any one of items 10-13, wherein the filter unit which is suitable for elution of said expression product from the filter unit after cell disruption in/on said filter unit is suitable to retain said disrupted host cell, thereby allowing passing through of and/or eluting said expression product.

17. The use of the filter unit of any one of items 9 and 11-13 or the system of any one of items 10-13, wherein the filter unit which is suitable for elution of said expression product from the filter unit after cell disruption in/on said filter unit is suitable to retain said expression product, thereby allowing passing through of and/or eluting said disrupted host cell.

18. The use of the filter unit of any one of items 9 and 11-13 or the system of any one of items 10-13, wherein said filter unit is suitable to separate the expression product from said host cell, thereby retaining said expression product and said disrupted host cell and allowing passing through of and/or eluting the expression product and/or the disrupted host cell.

19. The method of any one of items 1-8, use of any one of items 9 and 11-18 or the system of any one of items 10-18, wherein said expression product is a virus, preferably a virus selected from the group consisting of fowlpox virus, vaccinia virus and modified vaccinia virus Ankara (MVA).

20. The method, use or system of any of the preceding items wherein said cell-associated expression product is within or attached to the host cell.

21. The method, use or system of any of the preceding items, wherein said host cell is a vertebrate or insect cell, preferably an avian cell.

22. The method, use or system of any of the preceding items, wherein said host cell is cultured in suspension culture.

23. The method, use or system of any of the preceding items, wherein said culturing is in a disposable bio reactor, preferably in a wave bio reactor.

24. The method, use or system of any of the preceding items, wherein said host cell is disrupted in/on said filter unit by lysis, preferably hypotonic lysis.

25. The method, use or system of any of the preceding items, wherein the expression product is eluted for recovery.

26. The method, use or system of any of the preceding items, wherein the filter unit for collecting the host cell is a depth filter.

27. The method of any of the preceding items, further comprising a step of purifying said recovered expression product.

28. The method of item 27, wherein said purifying step includes a chromatography step selected from the group consisting of hydrophobic interaction chromatography, pseudo-affinity chromatography, anion exchange chromatography and/or size exclusion chromatography.

29. A method for the production of a pharmaceutical composition comprising the steps of the method of any one of items 1-8 and 19-28 further comprising a step of formulating the expression product recovered by said method with a pharmaceutically acceptable carrier.

30. An expression product obtainable by the method of any of items 1-8 or 19-28.

The following examples are included to further illustrate the invention by means of certain embodiments of the invention, and are not to be construed to limit the scope of the present invention in any way.

1. Upstream Processing

Fertilized chicken eggs are incubated for 12 days. After disinfection of the egg shell, the eggs are opened and the embryos are removed and stored in PBS (Phospate Buffered Saline). Embryos are decapitated and washed twice with PBS (10 ml/embryo) and once with trypsin (4 ml/embryo) for 5-6 minutes. 50 embryos each are incubated stirring in trypsin (30 ml/embryo) for 90 minutes at room temperature. At the end of trypsination, CEF-cells (chicken embryonic fibroblast) are filtrated through a 265 µm polyester mesh.

Filtrated CEF-cells are centrifuged at 470 g for 7 minutes at 20° C., pellets are resuspended in PBS. After additional centrifugation at the same settings, pellets are again resuspended in PBS, followed by a third centrifugation and resuspension of the CEF-cells in VP-SFM (Virus Propagation Serum Free Medium), 10 ml VP-SFM/embryo.

For wave incubation, VP-SFM supplemented with 4 mM L-Glutamine, 0.01% Pluronic and Gentamicin (100 µg/ml) is used, 20 L of VP-SFM are incubated in a 50 L wave bag. CEF-cells are seeded at $2\times10^6$ cells/ml into the supplemented VP-SFM, followed by addition of viral material at 0.1 pfu/cell. Wave bags are incubated at 37° C., 13 rocks/min, 8° angle, 400 ml/min airflow and 5% $CO_2$ for 90 h (some parameters are depending on viral construct).

2. Downstream Processing

At the end of wave incubation, wave bags containing virus, cells and growth medium are disconnected from the wave system. The complete content of the wave bags is pumped through a depth filter, without any additional processing. Depth filters are rinsed with TBS pH 7,7 (10 mM Tris, 140 mM NaCl) prior to use. One depth filter with 0.6 $m^2$ active filtration area, 3 µm pore size, Polypropylene, is used for 20 L of virus harvest. In this process step, the cellular material including the cell-associated viral material is retained on the depth filter.

Flow through, containing growth medium, released viral material and impurities, is discarded. At the end of this process step, depth filters are not allowed to drain. In order to remove remaining cell culture medium and impurities, each depth filter is rinsed with 1 L of lysis-buffer (1 mM Tris pH 9.0), flow through is discarded. Depth filters are not allowed to drain.

Hypotonic lysis is performed by flushing each depth filter with 20 L of lysis buffer (1 mM Tris pH 9.0) within 90 minutes.

3. Comparison with the Prior Art

The principle of hypotonic lysis of cells had to be transferred from cultivation in roller flasks to cultivation in wave bags in order to obtain a vaccine with comparable impurity profile.

Prior art processes for the production of, for example, PROSTVAC™ V/F include a hypotonic lysis step. After cultivation of virus-infected cells in roller flasks, cell culture medium is removed, whereas the CEF-cells (Chicken Embryo Fibroblast cells) remain attached to the walls of the roller flasks. As most of the virus is found cell-associated, removal of cell culture medium does not remove virus, but reduces tremendously the amount of impurities contained within the cell culture medium. Subsequently, the CEF-cells are lysed by adding lysis buffer (1 mM Tris pH 9.0) into the roller flasks. After incubation of the roller flasks for a defined period, lysate is removed from the roller flasks, pooled and used in subsequent depth filtration process. This depth filtration step reduces additionally impurities from the viral material.

In contrast to the adherent growth of CEF-cells in roller flasks, CEF-cells in wave bags are grown in suspension and therefore do not attach to the wave bags. Prior to hypotonic lysis, CEF-cells therefore need to be concentrated to be able to remove excessive cell culture medium (containing the impurities). This concentration of CEF-cells could be achieved either by batch- or by flow-through centrifugation. Batch centrifugation includes open process steps not compliant with the GMP-principles of aseptic processing. Flow-through centrifugation does not remove the complete cell culture medium, because cells need to stay suspended to be able to remove them from the flow-through centrifuge at the end of centrifugation. If cell culture medium is not removed completely, reduced efficiency of hyptonic lysis would result in a final product with insufficient titer and elevated impurity level.

It is known that cells in suspension could be collected on depth filters. Appropriate structure and pore size of the depth filters retains the cells in the filter-unit, whereas the cell culture medium passes the depth filter. However, it was surprisingly found that after this collection step, cells can be lysed directly on the depth filter using a lysis buffer as described above. Together with the lysis buffer the virus is eluted and further processed down-stream.

Virus-infected CEF-cells after upstream processing were pumped through depth filters, flow through (cell culture medium) was discarded (first reduction of impurities). CEF-cells on depth filters were lysed by pumping lysis buffer (1 mM Tris, pH 9.0) at a defined flow rate through the depth filters, lysate was collected for subsequent downstream processing (second removal of impurities).

Determination of virus content after lysis and depth filtration step revealed a comparable titer combined with a significantly reduced impurity profile, compared to alternative manufacturing process using ultrasonication to homogenize CEF-cells in cell culture medium.

The principle is applicable to other cell types than CEF-cells used in biotechnological production as well (e.g. immortalized avian and other cell lines).

The invention claimed is:

1. A method for recovering a poxvirus from a host cell comprising
   a. culturing the host cell under conditions that allow expression of the poxvirus;
   b. collecting the host cell in or on a filter unit;
   c. disrupting the host cell retained in or on the filter unit; and
   d. separating the poxvirus from the disrupted host cell.

2. The method of claim 1, wherein the poxvirus is selected from the group consisting of fowlpox virus, vaccinia virus, and modified vaccinia virus Ankara (MVA).

3. The method of claim 2, wherein the filter unit comprises a pore size of less than 10 μm.

4. The method of claim 1, wherein the poxvirus is a recombinant poxvirus.

5. The method of claim 1, wherein the host cell is a vertebrate or an insect cell.

6. The method of claim 5, wherein the vertebrate cell is an avian cell.

7. The method of claim 5, wherein the host cell is cultured in suspension culture.

8. The method of claim 5, wherein the host cell is cultured in a disposable bioreactor.

9. The method of claim 8, wherein the disposable bioreactor is a wave bioreactor.

10. The method of claim 1, wherein the host cell is disrupted in or on the filter unit by lysis.

11. The method of claim 10, wherein the lysis is hypotonic lysis.

12. The method of claim 1, wherein the expression product is eluted for recovery.

13. The method of claim 1, wherein the filter unit for collecting the host cell is a depth filter.

14. The method of claim 1, further comprising a step of purifying the recovered expression product.

15. The method of claim 14, wherein the purifying step includes a chromatography step selected from the group consisting of hydrophobic interaction chromatography, pseudo-affinity chromatography, anion exchange chromatography and size exclusion chromatography.

16. The method of claim 15, further comprising a step of formulating the recovered expression product with a pharmaceutically acceptable carrier.

* * * * *